US012622857B2

(12) United States Patent
Hernández Navarro et al.

(10) Patent No.: US 12,622,857 B2
(45) Date of Patent: May 12, 2026

(54) SKIN LIGHTENING COMPOSITION

(71) Applicant: BELLA AURORA LABS, S.A., Barcelona (ES)

(72) Inventors: Sergi Hernández Navarro, Barcelona (ES); Jordi Segura Tejedor, Barcelona (ES)

(73) Assignee: BELLA AURORA LABS, S.A., Barcelona (ES)

( * ) Notice: Subject to any disclaimer, the term of this patent is extended or adjusted under 35 U.S.C. 154(b) by 953 days.

(21) Appl. No.: 17/642,082

(22) PCT Filed: Jul. 6, 2020

(86) PCT No.: PCT/EP2020/068973
§ 371 (c)(1),
(2) Date: Mar. 10, 2022

(87) PCT Pub. No.: WO2021/052647
PCT Pub. Date: Mar. 25, 2021

(65) Prior Publication Data
US 2023/0124126 A1     Apr. 20, 2023

(30) Foreign Application Priority Data
Sep. 16, 2019     (EP) ..................................... 19382797

(51) Int. Cl.
| | |
|---|---|
| *A61K 8/11* | (2006.01) |
| *A61K 8/14* | (2006.01) |
| *A61K 8/44* | (2006.01) |
| *A61K 8/49* | (2006.01) |
| *A61K 8/60* | (2006.01) |
| *A61K 8/9789* | (2017.01) |
| *A61K 8/9794* | (2017.01) |
| *A61Q 19/02* | (2006.01) |

(52) U.S. Cl.
CPC .............. *A61K 8/4973* (2013.01); *A61K 8/11* (2013.01); *A61K 8/14* (2013.01); *A61K 8/44* (2013.01); *A61K 8/498* (2013.01); *A61K 8/602* (2013.01); *A61K 8/9789* (2017.08); *A61K 8/9794* (2017.08); *A61Q 19/02* (2013.01)

(58) Field of Classification Search
None
See application file for complete search history.

(56) References Cited

FOREIGN PATENT DOCUMENTS

| | | | |
|---|---|---|---|
| EP | 2842607 A1 | 3/2015 | |
| EP | 2789369 B1 * | 6/2018 | .......... A61K 31/365 |
| FR | 2975906 A1 | 12/2012 | |
| WO | 2008155048 A | 12/2008 | |
| WO | 2014170239 A1 | 10/2014 | |
| WO | 2015075116 A2 | 5/2015 | |

OTHER PUBLICATIONS

J. M. Gillbro, "The melanogenesis and mechanisms of skin-lightening agents—existing and new approaches", Journal, 2011, 210-221, vol. 33, International Journal of Cosmetic Science.
Sulekha Kumari, "Melanogenesis Inhibitors", Article, 2018, 924-931, vol. 98, Acta Derm Venereol.
Christina L. Burnett, "Final Report of the Safety Assessment of Kojic Acid as Used in Cosmetics", Journal, 2010, 244S-273S, vol. 29, International Journal of Toxicology.
D. Knoth, "Nanocarrier-Based Formulations: Production and Cosmeceutic Applications", Journal, 333-360, Cosmetic Formulation.
Samaneh Zolghadri, "A comprehensive review on tyrosinase inhibitors", Journal, 2019, 279-309, vol. 34, No. 1, Journal of Enzyme Inhibition and Medicinal Chemistry.
Sophie Drouillard, "Structure of an Amino Acid-Decorated Exopolysaccharide Secreted by a Vibrio alginolyticus Strain", Journal, 2015, 6723-6739, vol. 13, Marine Drugs.
Heather A. E. Benson, "Cosmetic Formulation Principles and Practice", Index, 2019, 1-4, table of contents only.
Florent Sahuc, "Reconstructed Human Pigmented Epidermis (RHPE): An in vitro model for the evaluation of melanogenesis", Paper, 2009, 1-6, Sofw Rhpe.
Ichiro Shirasugi, "Sulforaphane Inhibited Melanin Synthesis by Regulating Tyrosinase Gene Expressing in B16 Mouse Melanoma Cells", Journal, 2010, 579-582, vol. 74, No. 3, Biosci. Biotechnol. Biochem.

* cited by examiner

*Primary Examiner* — Fred H Reynolds
(74) *Attorney, Agent, or Firm* — Hayes Soloway PC

(57)     ABSTRACT
The present invention relates to a cosmetic skin lightening composition comprising the combination of sclareolide, kojic acid and ascorbyl glucoside, wherein kojic acid is encapsulated within a targeted microcapsule or nanocapsule having a melanocortin 1 receptor (MC1R) agonist peptide bound to the surface. It was found that such combination of active substances provided synergistic kin-whitening effect. The present invention also relates to the cosmetic use of this composition for skin whitening, particularly, for the elimination or reduction of hyperpigmented marks of the skin, such as UV exposure related marks, post-scar marks, post-inflammation marks, melasma marks, lentigo marks or age-related marks.

16 Claims, 2 Drawing Sheets

SKIN LIGHTENING COMPOSITION

CROSS-REFERENCE TO RELATED APPLICATIONS AND PRIORITY

This patent application claims priority from PCT Application No. PCT/EP2020/068973 filed Jul. 6, 2020, which claims priority from European Patent Application No. 19382797.9 filed Sep. 16, 2019. Each of these patent applications are herein incorporated by reference in their entirety.

TECHNICAL FIELD

The present invention relates to a cosmetic composition useful for skin lightening, particularly, for removing dark spots and marks from the skin.

STATE OF THE ART

Melanin is a dark pigment which is responsible for skin colour and is synthesized in melanocytes, a type of cells found in the epidermis. Specifically, melanogenesis takes place within the melanosomes, which are vesicles inside the melanocytes. A key enzyme of melanogenesis is tyrosinase, a glycoprotein located in the membrane of the melanosomes, which catalyses two steps of the synthesis of melanin from L-tyrosine. Other two enzymes involved in melanogenesis are tyrosinase-related protein 1 (Tyrp1) and tyrosinase-related protein 2 (Tyrp2). Two types of melanin are produced: brownish black eumelanin and reddish yellow pheomelanin.

Melanogenesis is a complex process which is regulated by a series of multistep signal transduction cascades and is influenced by a variety of extrinsic and intrinsic factors.

Thus, for example, UV exposure induces activation of p53, which in turn induces increased expression of POMC (proopiomelanocortin), which is then cleaved into small peptides such as ACTH (adrenocorticotropic hormone), α-, β-, and γ-MSH (melanocyte-stimulating hormone). ACTH and α-MSH stimulate the melanocortin-1 receptor (MC1R) on melanocytes, resulting in increased production of melanin. Furthermore, UV radiation enhances the production of reactive oxygen species (ROS) in keratinocytes and melanocytes, and a high concentration ROS causes DNA damage, further activating p53, and thus triggering melanogenesis.

The synthesis of melanin is also intrinsically regulated through microphthalmia-associated transcription factor (MITF) which regulates the key melanogenic enzymes tyrosinase, Tyrp1 and Tyrp2, and its activity is regulated by a number of signalling pathways, for example, cAMP, ERK/MAPK and NO/cGMP.

As a result of this complex process, the synthesis of melanin may be activated by different stimuli, for example, solar radiation, inflammation, acne, stress, hormonal changes, pollution or inflammatory processes, among others. The pigmentation that occurs as a sequela of cutaneous inflammation is generally known as post-inflammatory hyperpigmentation (PI).

The melanin generated in the melanocytes is transferred to neighbouring keratinocytes, thus the pigment becomes visible in the epidermis surface and becomes progressively darker due to photooxidation.

While melanin plays a key role in protecting the skin from harmful ultraviolet (UV) radiation, abnormally high production and accumulation of melanin in the skin can lead to hyperpigmentation. Although it is usually harmless, hyperpigmentation of the skin, especially on the face, such as melasma, solar lentigines and freckles, is generally considered unsightly. Thus, the concern about skin appearance has boosted the research into skin whitening cosmetic products, which are able to reduce skin pigmentation. These products are generally used to eliminate different kinds of pigment spots on the skin, or to lighten a naturally dark skin colour or to prevent skin pigmentation.

The mechanisms involved in skin pigmentation and the main skin-whitening agents available are disclosed, for example, in Gillbro et al., *The melanogenesis and mechanisms of skin-lightening agents—existing and new approaches*, Int. J. Cosm. Sci., 2011, 33, 210-221 or in Kumari et al., Melanogenesis inhibitors, Acta Derm. Venereol., 2018, 98, 924-931.

The most common approach for the whitening and depigmentation of skin is to reduce the melanin production by means of tyrosinase inhibition. Among the known tyrosinase inhibitors useful for skin-lightening are, for example, hydroquinone and its derivatives arbutin and deoxyarbutin, which show inhibition of melanogenesis, though their use may cause melanocyte cytotoxicity. Kojic acid, which is a naturally occurring fungal metabolite obtained from several species of fungi, such as *Aspergillus, Acetobacter* and *Penicillium*, is successfully used for treating melasma, though it can cause several adverse effects, such as contact dermatitis, sensitization and erythema. Azelaic acid (nonanedioic acid) is another tyrosinase inhibitor also commonly used as depigmenting agent. Also, polyphenols such as resveratrol or isoflavones such as glabridin, have been reported to have skin-lightening effects through tyrosinase inhibition.

Another approach used for skin-lightening is the inhibition of the transfer of mature melanosomes containing melanin to the keratinocytes. Some skin-lightening substances which are believed to act through this mechanism are protease-activated receptor 2 (PAR-2) inhibitors, such as soymilk and soybean extracts, and niacinamide.

Antioxidants are also commonly used for skin lightening, as they can neutralize reactive oxygen species (ROS) in the skin (which activate melanogenesis) and can also reduce the direct photooxidation of pre-existing melanin. Among the antioxidants commonly used as skin-lightening agents are vitamin E, vitamin B, vitamin C and ascorbic acid derivatives, such as magnesium ascorbyl phosphate, ascorbyl palmitate, and ascorbyl glucoside, for example.

The international patent application WO-A-2014/170239 discloses the use as skin-lightening agent of sclareolide, which is a naturally occurring substance found, for example, in *Salvia sclarea* L. The mechanism involved in the skin-lightening effect of sclareolide is related to its anti-inflammatory activity as Interleukin 1 (IL-1) alpha biosynthesis inhibitor, by inhibiting post-inflammatory hyperpigmentation. Furthermore, it was found that the combination of sclareolide with the tyrosinase inhibitor phenylethyl resorcinol provided synergistic in vitro melanin inhibition.

On the other hand, the patent application WO-A-2008/155048 discloses the combination of sclareolide and hesperidin methyl chalcone (HMC) for the tanning of the skin, for darkening the hair and for enhancing the synthesis of melanin.

Despite the substances and compositions for skin lightening described so far in the prior art, there is still the need for improved products, which provide safe and effective depigmentation of the skin. In particular, in order to have safer compositions, devoid of undesirable adverse and toxic effects, it would be desirable to provide improved combinations of skin-lightening cosmetic agents possessing strong antimelanogenic synergistic effect, in order to achieve improved depigmentation effect using reduced amounts of active ingredients.

OBJECT OF THE INVENTION

The object of the present invention is a skin-lightening composition.

Another aspect of the invention is the non-therapeutic cosmetic use of said composition for whitening the skin.

DETAILED DESCRIPTION OF THE INVENTION

Figure 1:
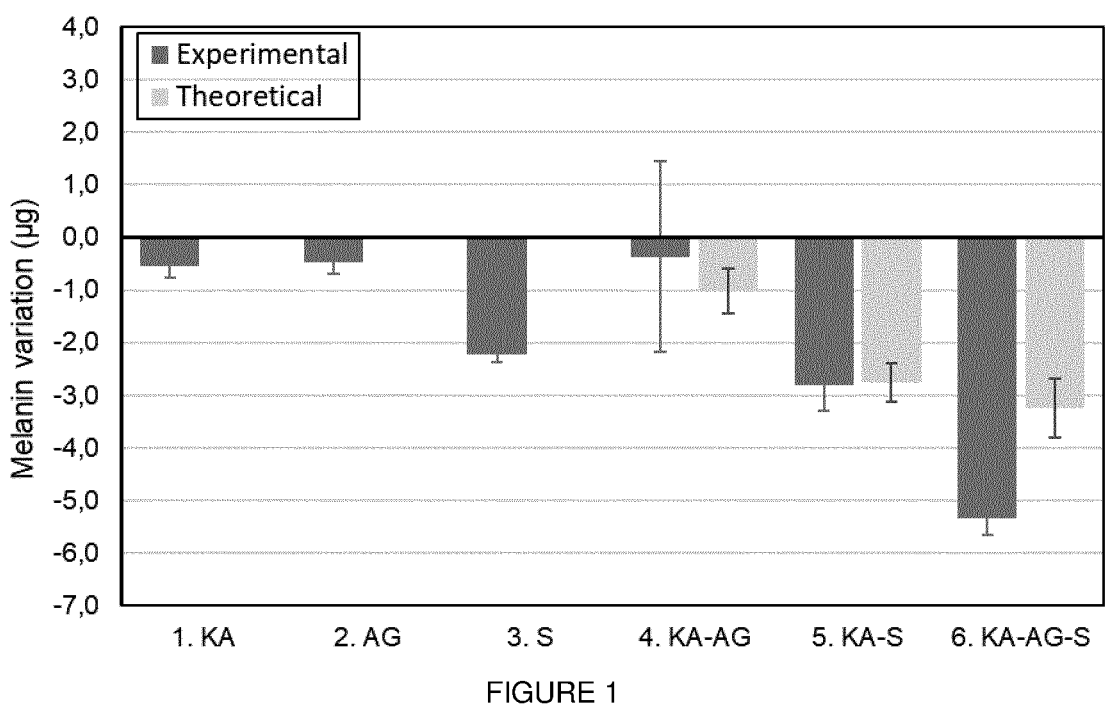
FIG. 1 shows a graph that represents the results of the in vitro depigmentation assay of example 5 using the RHPE model ("Reconstructed human pigmented epidermis"), wherein several compositions were topically applied once daily for 5 consecutive days on cultured pigmented keratinocytes (obtained by culturing normal human keratinocytes in the presence of melanocytes) and the melanin content was measured, before and after the treatment: y-axis shows the melanin content variation (in µg) after the treatment period and the x-axis shows the different compositions assayed (1—kojic acid, 2—ascorbyl glucoside, 3—sclareolide, 4—kojic acid and ascorbyl glucoside, 5—kojic acid and sclareolide and 6—kojic acid, ascorbyl glucoside and sclareolide). The dark-grey bars show the results obtained experimentally. For the combined compositions, the light-grey bars show the theoretical results that would be expected with a simple additive effect of the components of the combination.

The object of the present invention is a skin-lightening composition comprising:
(a) sclareolide;
(b) kojic acid; and
(c) ascorbyl glucoside;
wherein kojic acid is encapsulated within a microcapsule or nanocapsule comprising a peptide of formula (I):

R₂-Ser-Tyr-Ser-Nle-Glu-His-DPhe-Arg-(AA)-Gly-
    Lys-DPro-Val-R₁                                    (I)

4 wherein:
R$_1$ is the radical —NH—(CH$_2$)$_3$—O—(CH$_2$CH$_2$O)$_n$—(CH$_2$)$_3$—NH$_2$, wherein n is an integer from 1 to 10;
R$_2$ is selected from (C$_{1-24}$ alkyl)-CO—, (C$_{2-24}$ alkenyl)-CO— and (C$_{6-10}$ aryl)-CO—; and
AA is an amino acid containing an aromatic group;
and cosmetically acceptable salts and solvates thereof,
wherein the peptide is coupled to the outer surface of the microcapsule or nanocapsule.

The authors of the present invention have developed a cosmetic composition comprising the combination of sclareolide, kojic acid and ascorbyl glucoside that, surprisingly, provides enhanced synergistic whitening effects, allowing for the preparation of efficient skin-lightening compositions with reduced amounts of whitening active agents, thus minimizing the risk of any adverse effect.

Along the present description, as well as in the claims, the singular expressions, generally preceded by the articles "a", "an" or "the", are meant to include also the plural forms, unless the context clearly indicates otherwise. All percentages are expressed by weight, unless specifically stated otherwise. Numeric values preceded by the term "about" are meant to include also a certain variation around such value, namely a variation or ±5% of the stated amount. Numeric ranges defined by lower and upper endpoints are meant to include also said stated endpoints and they also include any narrower sub-range.

A cosmetic active agent or cosmetic active ingredient is any substance intended to be applied on the body surface, particularly on the skin, hair or nails, to provide a cosmetic effect. A cosmetic effect relates to beautify and/or improve the feeling or sensory aspects of normal, nondiseased skin, hair or nail. Dry skin would be included in this category. Cosmetic effects do not involve any therapeutic effect, i.e., cosmetics are not intended to prevent or ameliorate any disease.

A cosmetic effect is, for example, the whitening of skin. The terms "whitening", "lightening", or "depigmentation" are used interchangeably herein and are referred to the process of lightening hyperpigmented skin, typically, to eliminate or reduce dark spots, blemishes or marks of the skin, including age spots, post-acne marks, uneven skin tone, post-inflammatory hyperpigmentation or melasma and lentigo spots, for example. In the present description, the terms "spots", "marks" and "blemishes" are meant to be equivalents and are used interchangeably.
Kojic Acid Kojic acid is a natural product produced by several species of fungi of the *Aspergillus* and *Penicillum* genus, including, among others, *A. oryzae, A. flavus, A. tamarii* and *A. parasiticus*, and is chemically designated as 5-hydroxy-2-(hydroxymethyl)-4H-pyran-4-one (CAS number 501-30-4).

Kojic acid can be produced by fermentation, using suitable *Aspergillus* kojic acid producing strains, and using a variety of carbon and nitrogen sources, as disclosed, for example, in Mohamad et al., *Kojic acid: applications and development of fermentation process for production*, Biotechnol. Mol. Biol. Rev., 2010, 5(2), 24-37. Kojic acid is commercially available from several sources, for example, Sigma-Aldrich, Spec-Chem Industry Inc, or Cosphatech LLC.

Kojic acid is a well-known tyrosinase inhibitor used in cosmetic compositions as skin-lightening agent. Kojic acid is used in cosmetic topical compositions at concentrations that may differ depending on the type of composition, intended use and also depending on the specific countries' regulations; for example, the content of kojic acid generally ranges from 0.1% to 2% in the skin-whitening compositions sold in U.S.A. or from 0.1% up to 30% in those sold in Canada (Brunett et al., *Final report of the safety assessment of kojic acid as used in cosmetics*, Int. J. Toxicol., 2010, 29 (Suppl. 4), 244S-273S).

In the compositions of the present invention, kojic acid is used in the form of targeted microcapsules or nanocapsules, i.e., capsules comprising a melanocortin 1 receptor (MC1R) agonist peptide on the surface, which selectively binds to melanocortin 1 receptors (MC1R) on the melanocytes, thus said capsules transport and deliver kojic acid specifically to the melanocytes, thus allowing to decrease the amount of kojic acid needed for effective skin-whitening effect. Additionally, the synergistic effect found for the specific combination of kojic acid, sclareolide and ascorbyl glucoside, also allows for a further reduced amount of kojic acid in the composition.

Therefore, the content of kojic acid in the composition of the present invention is generally in the range 0.0001%-0.1% (w/w), preferably in the range 0.0001%-0.01% (w/w), more preferably in the range 0.0001%-0.001% (w/w), still more preferably in the range 0.0003%-0.0009% (w/w), still more preferably in the range 0.0004%-0.0008% (w/w), and still more preferably in the range 0.0005%-0.0007% (w/w).

Or in other words, the content of kojic acid in the composition of the present invention is generally in the range 1 ppm-1000 ppm, preferably in the range 1 ppm-100 ppm, more preferably in the range 1 ppm-10 ppm, still more preferably in the range 3 ppm-9 ppm, still more preferably in the range 4 ppm-8 ppm, and still more preferably in the range 5 ppm-7 ppm.

Encapsulated Kojic Acid

In the composition of the present invention, kojic acid is encapsulated within a microcapsule or nanocapsule. These microcapsules or nanocapsules have attached on the outer surface thereof a peptide of formula (I) which is a melanocortin 1 receptor (MC1R) agonist and are thus designed for the targeted delivery of the encapsulated actives to melanocytes. Said targeted capsules employed are disclosed in the patent application WO-A-2015/075116.

The microcapsules or nanocapsules, which also generally referred to herein as "capsules", have typically a size distribution from 10 nm to 10000 nm, preferably from 50 nm to 5000 nm, more preferably from 100 nm to 1000 nm, still more preferably from 150 nm to 450 nm, and still more preferably from 180 nm to 400 nm, as disclosed in WO-A-2015/075116 op. cit. The size of the microcapsules may be determined by Scanning Electron Microscopy (SEM).

The microcapsules are preferably polymeric, generally made of one or more biodegradable polymers.

In one embodiment, the polymers forming the capsules are selected from the group consisting of poly(D,L-lactide-co-glycolide), polylactic acids, poly(propylene fumarate-co-ethylene glycol) [P(PF-co-EG)] block copolymer, poly-anhydride poly(fumaric-co-sebacic) anhydride, poly(ethylene oxide)-poly(lactide/glycolide), polyvinyl alcohol, alginate, dextran, chitosan, hydroxyapatite, collagen, fibrin, hyaluronic acid, carbomers, poly(ethylene glycol), and mixtures thereof.

It is required that at least one of the polymers forming the capsule bears carboxylic groups for binding the peptide of formula (I), by coupling said carboxylic groups with the amine terminal groups in $R_1$.

In one embodiment, the microcapsules are bilayered polymeric microcapsules which comprise a core polymer (or "inner layer polymer"), and an outer shell polymer (or "outer layer polymer").

The core polymers and the outer shell polymers are preferably selected from the group consisting of poly(D,L-lactide-co-glycolide), polylactic acids, poly(propylene fumarate-co-ethylene glycol) [P(PF-co-EG)] block copolymer, poly-anhydride poly(fumaric-co-sebacic) anhydride, poly(ethylene oxide)-poly(lactide/glycolide), polyvinyl alcohol, alginate, dextran, chitosan, hydroxyapatite, collagen, fibrin, hyaluronic acid, carbomers, poly(ethylene glycol), and mixtures thereof.

In a preferred embodiment the core polymer and the outer shell polymer are different. In a more preferred embodiment, the core polymer is poly(D,L-lactide-co-glycolide) (PLGA) and the outer shell polymer is polyvinyl alcohol (PVA). In a more preferred embodiment, PLGA has a lactide/glycolide molar ratio from 40:60 to 60:40, more preferably 50:50.

The preparation of said microcapsules or nanocapsules is disclosed in WO-A-2015/075116, and generally involves the mixture of the cosmetic active ingredient and the polymer(s) forming the capsule in a suitable solvent.

When the capsules are bilayered microcapsules or nanocapsules, the preparation process typically comprises:

a) mixing the inner layer polymer with kojic acid in a suitable solvent, wherein the solvent is, for example, acetone, acetonitrile, dichloromethane (DCM), ethanol, methanol, chloroform, dimethylformamide (DMF) or ethyl acetate;

b) emulsifying the mixture obtained in step a) with the outer layer polymer in a suitable solvent, wherein the solvent is, for example, water, acetonitrile, dichloromethane (DCM), ethanol, methanol, chloroform, dimethylformamide (DMF), dimethylsulfide (DMS) or ethyl acetate, preferably the solvent is selected from water, ethanol, methanol, dimethylformamide, and dimethylsulfide and more preferably the solvent is water; and optionally c) isolating the capsules.

A further step in the preparation of the targeted capsules of the invention is the coupling of the peptide of formula (I), which confers affinity towards melanocytes, to the outer surface of the microcapsule or nanocapsule. This step can be performed before or after forming the capsule, preferably after forming the capsule.

This coupling step is performed by coupling the carboxyl groups present on the surface of the capsules and the amino terminal group of the peptide to form an amide bond.

Said carboxyl groups present on the surface of the capsules may belong either to the outer shell polymer or to the inner shell polymer but still present outside the surface of the microcapsule or nanocapsule. In a preferred embodiment the covalent bond is an amide bond between the peptide's amino terminal group (in the $R_1$ group) and the carboxyl group from the PLGA polymer present outside of the surface. Preferably, the outer shell polymer is polyvinyl alcohol.

Preferably, for performing the coupling reaction, the carboxyl groups on the surface of the capsules are previously activated.

The peptide of formula (I) is as follows:

$$R_2\text{-Ser-Tyr-Ser-Nle-Glu-His-DPhe-Arg-(AA)-Gly-Lys-DPro-Val-}R_1 \qquad (I)$$

wherein:

$R_1$ is the radical $-NH-(CH_2)_3-O-(CH_2CH_2O)_n-(CH_2)_3-NH_2$, wherein n is an integer from 1 to 10;

$R_2$ is selected from $(C_{1-24}$ alkyl)-CO—, $(C_{2-24}$ alkenyl)-CO— and $(C_{6-10}$ aryl)-CO—; and AA is an amino acid containing an aromatic group; and cosmetically acceptable salts and solvates thereof.

In the above peptide sequence, the amino acids mentioned without specifying their stereochemistry (Ser, Tyr, Nle, Glu, His, Arg, Gly, Lys and Val) are meant to include both the D and the L stereoisomers, while DPhe and DPro designate specifically the D stereoisomers of Phenylalanine and Proline, respectively.

In one embodiment of the invention, the amino acids Ser, Tyr, Nle, Glu, His, Arg, Gly, Lys and Val in the above sequence designate specifically the L stereoisomers only.

$R_1$ is the radical —NH—$(CH_2)_3$—O—$(CH_2CH_2O)_n$—$(CH_2)_3$—$NH_2$, wherein n is an integer from 1 to 10, preferably n is an integer from 1 to 3, and more preferably is 1 or 2. In one embodiment, n is 1 and $R_1$ derives from ethylene glycol bis(3-aminoproyl) ether (CAS 2997-01-5). In another embodiment, n is 2 and $R_1$ derives from diethylene glycol bis(3-aminoproyl) ether, also called 4,7,10-trioxa-1,13-tri-decanediamine (CAS 4246-51-9).

The term "$C_{1-n}$ alkyl" means a linear or branched alkyl group having from 1 to n carbon atoms. The term $C_{2-n}$ alkenyl means a linear or branched hydrocarbon chain radical having one or more carbon-carbon double bonds and having from 2 to n carbon atoms. The term $C_{6-10}$ aryl means a mono- or a bicyclic aromatic group having from 6 to 10 carbon ring atoms, such as phenyl, naphthyl or indenyl. The $C_{6-10}$ aryl group may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

In the peptide of formula (I) $R_2$ is selected from $(C_{1-24}$ alkyl)-CO—, $(C_{2-24}$ alkenyl)-CO— and $(C_{6-10}$ aryl)-CO—, preferably $R_2$ is $(C_{1-24}$ alkyl)-CO—, more preferably $R_2$ is $(C_{1-16}$ alkyl)-CO—, still more preferably $R_2$ is selected from acetyl, propanoyl, pentadecanoyl, hexadecanoyl and heptadecanoyl, and still more preferably $R_2$ is hexadecanoyl (also called palmitoyl).

In the peptide of formula (I) AA is an amino acid containing an aromatic group. Such amino acid may be a natural amino acid or a synthetic amino acid. In one embodiment, AA is selected from tryptophan, 3-(2-naphthyl)-D-alanine, 3-amino-3-(1-naphthyl)-propionic acid, 3-amino-3-(biphenyl)-propionic acid, phenylalanine, tyrosine, histidine, 5-hydroxytryptophan and L-3,4-dihydroxy-phenylalanine, preferably AA is selected from tryptophan, phenylalanine, tyrosine and L-3,4-dihydroxyphenylalanine, more preferably AA is tryptophan, and still more preferably is L-tryptophan.

The cosmetically acceptable salts and solvates of the peptide of formula (I) can also be used for preparing the microcapsules or nanocapsules of the compositions of the present invention. The term "cosmetically acceptable" means that those salts or solvates that are generally admitted as safe and suitable for its use in animals and more particularly in human beings. The pharmaceutically acceptable salts include addition salts, such as base addition salts, for example, metal salts (such as lithium, sodium, potassium, etc), organic amines (such as ethylamine, diethylamine, ethylenediamine, etc), or basic amino acids (such as arginine, lysine or histidine), or acid addition salts, for example, with organic acids (such as the acetate, citrate, lactate or tartrate salts, among others), or inorganic acids (such as chloride, sulphate, borate or carbonate salts, among others). The cosmetically acceptable salts of the peptide of formula (I) can be obtained by conventional methods well known in the state of the art. The cosmetically acceptable solvates include, for example, hydrated forms.

In one embodiment, kojic acid is encapsulated within a microcapsule or nanocapsule comprising a peptide of formula (I):

$$R_2\text{-Ser-Tyr-Ser-Nle-Glu-His-DPhe-Arg-(AA)-Gly-Lys-DPro-Val-}R_1 \qquad (I)$$

wherein:

The amino acids Ser, Tyr, Nle, Glu, His, Arg, Gly, Lys, Val and AA may be in the L or D form, preferably they are all in the L form;

$R_1$ is the radical —NH—$(CH_2)_3$—O—$(CH_2CH_2O)_n$—$(CH_2)_3$—$NH_2$, wherein n is an integer from 1 to 10, preferably from 1 to 3, more preferably is 1 or 2;

$R_2$ is selected from $(C_{1-24}$ alkyl)-CO—, $(C_{2-24}$ alkenyl)-CO— and $(C_{6-10}$ aryl)-CO—, preferably $R_2$ is $(C_{1-24}$ alkyl)-CO—, more preferably $R_2$ is $(C_{1-16}$ alkyl)-CO—, still more preferably $R_2$ is selected from acetyl, propanoyl, pentadecanoyl, hexadecanoyl and heptadecanoyl, and still more preferably $R_2$ is hexadecanoyl;

AA is an amino acid containing an aromatic group, preferably is selected from tryptophan, 3-(2-naphthyl)-D-alanine, 3-amino-3-(1-naphthyl)-propionic acid, 3-amino-3-(biphenyl)-propionic acid, phenylalanine, tyrosine, histidine, 5-hydroxytryptophan and L-3,4-dihydroxy-phenylalanine, preferably is selected from tryptophan, phenylalanine, tyrosine and L-3,4-dihydroxyphenylalanine, more preferably AA is tryptophan, and still more preferably is L-tryptophan;

and cosmetically acceptable salts and solvates thereof, wherein the peptide is coupled to the outer surface of the microcapsule or nanocapsule.

Sclareolide

Sclareolide (CAS number 564-20-5) is a naturally occurring substance found in several plant sources, for example, in *Salvia sclarea L.*

It is also known as norambreinolide; or by the chemical name naphtho[2,1-b]furan-2(1H)-one, decahydro-3a,6,6,9a-tetramethyl, [3aR-(3aα,5aβ,9aα,9bβ]; or as (3aR,5aS,9aS, 9bR)-3a,6,6,9a-tetramethyl-1,4,5,5a,7,8,9,9b-octahydro-benzo[e][1]benzofuran-2-one (IUPAC).

Sclareolide may be obtained by extraction from some species of the *Salvia* genus, or it can be synthetically obtained as substantially pure sclareolide.

Sclareolide is commercially available from several sources, for example, from the company Sym rise.

The mechanism involved in the skin-lightening effect of sclareolide is related to its anti-inflammatory activity as Interleukin 1 (IL-1) alpha biosynthesis inhibitor, by inhibiting post-inflammatory hyperpigmentation, as disclosed in the international patent application WO-A-2014/170239.

The amount of sclareolide in the composition of the invention is generally comprised in the range 0.001%-5% (w/w), preferably comprised in the range 0.01%-2.5% (w/w), more preferably comprised in the range 0.05%-1% (w/w), still more preferably comprised in the range 0.1%-0.5% (w/w), and still more preferably is about 0.2% (w/w).

Optionally, sclareolide may be encapsulated in the form of liposomes. Liposomes are commonly used in cosmetic formulations for improving dermal penetration of actives. As is well known in the art, liposomes are spherical vesicles with sizes generally in the range between about 60 nm and 300 nm and are most often composed of phospholipids which form at least one phospholipid bilayer, but may also include other lipids. Liposomes contain hydrophilic cores in which hydrophilic actives may be encapsulated, while hydrophobic actives are incorporated in the bilayer, so liposomes are suitable carriers for both hydrophilic and lipophilic actives (Knoth et al., *Nanocarrier-Based Formulations: Production and Cosmeceutic Applications*, in: *Cosmetic Formulation. Principles and Practice*, Benson H. A. E., Roberts M. S., Rodrigues Leite-Silva V. and Walters K. A., editors, CRC Press, 2019). Liposomes may be prepared by well-known techniques; in general, the preparation methods involve mixing the membrane-forming lipids, in an organic phase, drying, subsequent hydration of the lipids and further size reduction by different mechanical treatment such as sonication, extrusion or homogenization.

Sclareolide, which is a hydrophobic active, is suitably added in the form of liposomes to water-based formulations, such as o/w emulsions.

Furthermore, it was surprisingly found that the compositions of the invention showed improved cellular viability and depigmentation efficacy in an in vitro model for evaluation of melanogenesis (RHPE: Reconstructed human pigmented epidermis) when sclareolide was in the form of liposomes (see example 7). It was found that, by using liposomes, it was possible to reduce the amount of sclareolide in the formulation to achieve an equivalent depigmenting effect.

Therefore, in one embodiment of the invention, sclareolide is encapsulated in the form of liposomes. Preferably, the amount of sclareolide in the composition when sclareolide is in the form of liposomes is comprised in the range 0.01%-2.5% (w/w), more preferably comprised in the range 0.01%-0.5% (w/w), still more preferably comprised in the range 0.03%-0.2% (w/w), and still more preferably is about 0.1% (w/w).

Ascorbyl Glucoside

Ascorbyl glucoside, also known as L-ascorbic acid 2-glucoside (CAS 129499-78-1) is a derivative of vitamin C (L-ascorbic acid) wherein the C2-hydroxyl group of L-ascorbic acid is bound to a molecule of glucose. Once permeated into the skin, ascorbyl glucoside is broken down into L-ascorbic acid and glucose by the enzyme alpha-glucosidase, thus gradually delivering vitamin C to the skin.

Ascorbyl glucoside is widely available from several suppliers, for example, from the companies DKSH, Spec-Chem Industry Inc, or Cosphatech LLC.

Ascorbyl glucoside is used in skin-lightening compositions. Its whitening effect is related to the antioxidant properties of vitamin C, so it is able to neutralize reactive oxygen species (ROS) in the skin (which activate melanogenesis) and can also reduce the direct photooxidation of pre-existing melanin.

The amount of ascorbyl glucoside in the cosmetic composition of the present invention is typically comprised between 0.01%-10% (w/w), preferably comprised between 0.1%-8% (w/w), more preferably comprised between 0.5%-5% (w/w), still more preferably comprised between 1%-3% (w/w), and still more preferably is about 2% (w/w).

Compositions of the Invention

Additional Active Ingredients

In one embodiment, the composition of the invention does not contain any additional skin-whitening active substance, and essentially consists of kojic acid, sclareolide and ascorbyl glucoside. The term "essentially consists" means that the composition optionally contains formulation vehicle (s) and additional formulation additives, but does not contain further skin-whitening cosmetically active substances.

In another embodiment, the composition of the invention contains additional skin-whitening active ingredients.

Any known skin-whitening active disclosed in the state of the art, either of natural or synthetic origin, and acting through any whitening mechanism may be suitable to be included in the composition as additional skin-whitening agent. Among the disclosed mechanisms for skin lightening are tyrosinase inhibition, MITF inhibition, inhibition of the transfer of melanin to keratinocytes or antioxidative mechanisms, among others.

For example, the skin-whitening substances disclosed in the following review articles could be used: Gillbro et al. op. cit.; Kumari et al. op. cit.; or Zolghadri et al., *A comprehensive review on tyrosinase inhibitors*, J. Enzyme Inhib. Med. Chem., 2019, 34 (1), 279-309.

Among the substances with tyrosinase inhibitory activity, as is well-known by the skilled in the art, are phenolic compounds such as hydroquinone, arbutin, deoxyarbutin, 4-(6-hydroxy-2-naphthyl)-1,3-bezendiol, resorcinol, 4-n-butylresorcinol, vanillin and its derivatives, 10'(Z)-heptadecenylhydroquinone, isotachioside and its glycoside derivatives. Also some flavonoid derivatives, mostly found in herbal plants, fruits and synthetic sources, are well-known as potent inhibitors of tyrosinase, belonging to the flavones (such as luteolin, apigenin, baicalein, chrysin, apigetrin, vitexin, baicalin, nobiletin, morusone or tangeretin, among others), flavonols (such as myricetin, kaempferol, quercetin, morin, isorhamnetin, galangin, rutin, quercitrin, or astragalin, among others), isoflavones (such as daidzein, genistein, glycitein, formononetin, genistin or daidzin, for example, some of them typically derived from soybean; or glabridin, isolated from the root of *Glycyrrhiza glabra*; among others), flavanones (such as naringenin, hesperetin, eriodictyol, naringin, hesperidin, or liquiritin, among others), flavanonols (such as taxifolin), flavanols (catechin, epicatechin, epigallocatechin, peicatechin gallate, epigallocatechin gallate or proanthocyanidins), anthocyanidins (cyanidin, delphinidin, malvidin, peonidin, or pelargonidin, among others), curcuminoids (curcumin or desmethoxycurcumin, for example), coumarins, chalcones (such as isoliquiritigenin, glabrene, 2,4,2',4'-hydroxycalcone, among others) or aurones (4,6,4'-trihydroxyaurone, among others) classes. Other polyphenols with tyrosinase inhibiting activity are, for example, resveratrol and oxyresveratrol. Other substances belonging to different chemical classes have been disclosed as tyrosinase inhibitors, such as some terpenes (for example, bakuchiol or some carvacrol derivatives), quinones (such as aloin, and aloesin, found in Aloe vera, or tanshinone), pyridine derivatives (e.g. ((S)-(5-(benzyloxy)-1-octyl-4-oxo-1,4-dihydropyridin-2-yl)methyl 2-amino-3-phenylpropanoate), retinoids (such as adapalene and tretinoin, among others), carboxylic acids (such as azelaic acid or cinnamic acid, for example), azoles or thiazolidine derivatives.

Some of the known tyrosinase inhibitors may be of synthetic origin, while most of them are derived from plants, available as plant extracts, or are produced by fungi or bacteria. In particular, a huge amount of plant species has been disclosed in the art to contain tyrosinase inhibiting substances.

Another skin-whitening active is sulforaphane, which can be found, for example, in broccoli and broccoli sprouts, as well as in extracts of cress (*Lepidium sativum*, also belonging to the Brassicaceae family), which inhibits melanogenesis by a mechanism involving the suppression of tyrosinase expression by modulating MAP kinase pathways (Shirasugi et al., *Suforaphane inhibited melanin synthesis by regulating tyrosinase gene expression in B16 mouse melanoma cells*, Biosci. Biotechnol. Biochem. 2010, 74 (3), 579-582). Furthermore, sulforaphane enhances proteasomal activity, which could contribute to reduce the accumulation of oxidized proteins and thus inhibit the formation of lipofuscin, which is another yellow-brown pigment responsible of lentigo age-related spots.

Another reported skin-whitening agent suitable to be used as additional active in the compositions of the present invention is a leaf extract from the Vietnamese tree Langsat or Duku (*Lansium domesticum*). The melanin-synthesis decreasing effect of this extract is related with an increase of the expression of the pigmentation gene silencer microRNA (miR-490-3p) which inhibits the synthesis of the tyrosinase enzyme.

Another suitable whitening substance is an extract from the Sea Lily or Sea Daffodil (*Pancratium maritimum*). It is believed that the melanin synthesis inhibiting effect of this extract may be due to its activity as inhibitor of the expression of POMC (proopiomelanocortin), which is involved in the activation of melanogenesis through the production of alpha-melanocyte-stimulating hormone (alpha-MSH).

Other type of skin-whitening substances suitable as additional actives in the composition of the invention are those whose mechanism of action is based on the inhibition of the transfer of mature melanosomes containing melanin to the keratinocytes, for example, protease-activated receptor 2 (PAR-2) inhibitors, such as soymilk and soybean extracts, or other substances such as niacinamide or saccharide isomerate, among others. Saccharide isomerate is a marine exopolysaccharide secreted by the Gram-negative marine bacteria *Vibrio alginolyticus* (CNCM 1-4994), comprising two amino acids within its structure. The structure and isolation process of saccharide isomerate is discussed in Drouillard et al., *Structure of an amino acid-decorated exopolysaccharide secreted by a Vibrio alginolyticus strain*, Mar. Drugs, 2015, 13, 6723-6739 and in the French patent application FR-A-2975906.

In one embodiment, the composition of the invention also comprises saccharide isomerate as additional skin-whitening active substance.

The compositions comprising additionally saccharide isomerate were found to be particularly effective for skin whitening, as found in the clinical study disclosed in example 7.

When present in the composition, the amount of saccharide isomerate is generally comprised in the range 0.00001%-2% (w/w), preferably in the range 0.00001%-1% (w/w), more preferably in the range 0.0001%-0.1% (w/w), and still more preferably in the range 0.001%-0.01% (w/w).

In one embodiment, the composition of the invention essentially consists of kojic acid, sclareolide, ascorbyl glucoside and saccharide isomerate, including the preferred amounts and forms as disclosed above, and does not contain any additional skin-whitening active substance.

In one embodiment, the composition of the invention additionally comprises isoflavones from soybeans, preferably comprises genistein.

When present in the composition, the amount of genistein is generally comprised in the range 0.00001%-2% (w/w), preferably in the range 0.00001%-1% (w/w), more preferably in the range 0.0001%-0.1% (w/w), and still more preferably in the range 0.001%-0.01% (w/w).

In one embodiment, the composition additionally comprises suforaphane, for example, as *Lepidium sativum* extract.

When present in the composition, the amount of sulforaphane is generally comprised in the range 0.00001%-2%

(w/w), preferably in the range 0.00001%-1% (w/w), more preferably in the range 0.0001%-0.1% (w/w), and still more preferably in the range 0.001%-0.01% (w/w).

In one embodiment, the composition of the invention additionally comprises both genistein and suforaphane. The depigmentation effect of those substances, added to the synergistic depigmentation provided by the sclareolide-kojic acid-ascorbyl glucoside combination, may be particularly useful against lentigo and age-related spots. Generally, the amount of genistein is comprised in the range 0.00001%-2% (w/w), preferably in the range 0.00001%-1% (w/w), more preferably in the range 0.0001%-0.1% (w/w), and still more preferably in the range 0.001%-0.01% (w/w); and the amount of sulforaphane is comprised in the range 0.00001%-2% (w/w), preferably in the range 0.00001%-1% (w/w), more preferably in the range 0.0001%-0.1% (w/w), and still more preferably in the range 0.001%-0.01% (w/w). Optionally, the composition comprises also saccharide isomerate, generally in an amount comprised in the range 0.00001%-2% (w/w), preferably in the range 0.00001%-1% (w/w), more preferably in the range 0.0001%-0.1% (w/w), and still more preferably in the range 0.001%-0.01% (w/w).

In one embodiment, the composition of the invention additionally comprises *Pancratium maritimum* extract. The depigmentation effect of this substance, as inhibitor of the expression of POMC (proopiomelanocortin), in combination with the synergistic depigmentation provided by the sclareolide-kojic acid-ascorbyl glucoside combination, may be particularly useful against spots produced by inflammatory processes.

When present in the composition, the amount of *Pancratium maritimum* extract is generally comprised in the range 0.00001%-2% (w/w), preferably in the range 0.00001%-1% (w/w), more preferably in the range 0.0001%-0.1% (w/w), and still more preferably in the range 0.001%-0.01% (w/w). Optionally, the composition comprises also saccharide isomerate, generally in an amount comprised in the range 0.00001%-2% (w/w), preferably in the range 0.00001%-1% (w/w), more preferably in the range 0.0001%-0.1% (w/w), and still more preferably in the range 0.001%-0.01% (w/w).

In one embodiment, the composition of the invention additionally comprises *Lansium domesticum* (Langstat) leaf extract. The composition according to this embodiment may be particularly useful against melasma hyperpigmentation, due to the additional melanin-synthesis inhibition provided by the Langstat extract through miR-490-3p.

When present in the composition, the amount of *Lansium domesticum* leaf extract is generally comprised in the range 0.0001%-5% (w/w), preferably in the range 0.0005%-1% (w/w), more preferably in the range 0.001%-0.5% (w/w), and still more preferably in the range 0.01%-0.1% (w/w). Optionally, the composition also comprises saccharide isomerate, generally in an amount comprised in the range 0.00001%-2% (w/w), preferably in the range 0.00001%-1% (w/w), more preferably in the range 0.0001%-0.1% (w/w), and still more preferably in the range 0.001%-0.01% (w/w).

Formulations

The composition of the invention typically comprises the active cosmetic ingredients and at least one dermatologically acceptable carrier or vehicle. A substance is considered to be "dermatologically acceptable" or "cosmetically acceptable" if it is suitable and non toxic for use in contact with human skin tissue.

The composition according to present invention may be in the form of cream, gel, lotion, paste, foam, solution, suspension, emulsion, milk, or stick preparation, for example.

Suitable carriers may be, for example, anhydrous, as mixtures of fats, waxes, animal and plant oils and solid and liquid hydrocarbons. Or the carrier may be water or an aqueous solution of hydrophilic substances. Preferably, the carrier is in the form of an emulsion. Emulsions may be, typically, oil-in-water emulsions, water-in-oil emulsions, water-in-oil-in-water, oil-in-water-in-oil or water-in-silicone emulsions. An emulsion may generally be described as having a continuous aqueous phase (oil-in-water and water-in-oil-in-water) or a continuous oil phase (water-in-oil and oil-in-water-in-oil). The oil phase may comprise silicone oils, non-silicone oils such as paraffin hydrocarbons, fatty alcohols, fatty acids, fatty acid esters, waxes or plant oils, or mixtures thereof. The aqueous phase may comprise water or a water solution of hydrophilic substances, such as polyols, alpha hydroxy acids, amino acids, protein hydrolysates, simple sugars, and polysaccharides.

Emulsifiers, which are common components of emulsions, are surface-active agents (surfactants) and include non-ionic surfactants, anionic surfactants, cationic surfactants and amphoteric surfactants. Non-ionic surfactants include, among others, ethoxylated fatty alcohols, ethoxylated fatty acid esters, alkyl glucosides or alkyl oligoglucosides, ethoxylated sorbitan fatty acid esters, monoglycerol/polyglycerol fatty acid esters, ethoxylated glycerin monesters, ethoxylated polyglyceryl esters, alkyl dimethylamine oxides, or poloxamers, among others. Anionic surfactants include alkaline soaps, alkyl sulphates, alkyl ether sulphates, alkyl sulphosuccinates, acyl sarcosinates or acyl isethionates, among others. Cationic surfactants include quaternary ammonium salts, or pyridine salts, among others. Amphoteric surfactants include imidazoline derivatives, betaines, amidobetaines and sulphobetaines.

Other common ingredients in the formulation are, for example, emollients, humectants, preservatives, viscosity controlling agents, antioxidants, pH regulators, UV filters, chelating agents, perfumes and colorants. Common emollients are, for example, paraffin hydrocarbons, silicones, fatty alcohols, fatty acids, esters of fatty acids with alcohols, triglycerides, ceramides, phospholipids and waxes. Humectants include polyhydroxy alcohols, proteins and hydroxyl acids. Common preservatives include sorbic acid and its salts, benzoic acid and its salts, parabens, imidazolidinyl urea, diazolidinyl urea, DMDM hydantoin, sodium hydroxymethylglycinate, methylchloroisothiazolinone/methylisothiazolinone, benzyl alcohol and 2-phenoxyethanol, among others. Other additives may also be added for controlling the viscosity of the formulation, for example, xanthan gum, gellan gum, carrageenans, pectin, starch derivatives, carbomers, cellulose derivatives (hydroxyethylcellulose, hydroxypropylcellulose, hydroxypropyl methylcellulose, methylcellulose, ethylcellulose, or carboxymethylcellulose, for example), polyamides, glutamides, colloidal silica or waxes (e.g. beeswax or vegetable waxes), among others.

The cosmetic composition of the invention has typically a slightly acidic pH, close to the physiological pH of the skin. Common acidity regulators are organic acids, including hydroxy acids and fatty acids. Some of the most common pH regulators in cosmetic emulsions are hydroxy acids such as lactic and citric acids.

The above cited ingredients, as well as many others suitable cosmetic formulation excipients, are well-known to the skilled in cosmetic formulation. Such cosmetic ingredients are commercially available from several companies, such as Comercial Química Massó, SA, Evonik, DuPont or Dow Corning, among others.

The preparation of the cosmetic composition is made according to procedures well-known to the skilled in cosmetic formulation, generally involving simple steps of mixing, and optionally heating the component ingredients.

The description of the main cosmetic ingredients and procedures may be found, for example, in: *Cosmetic Formulation. Principles and Practice*, Benson H. A. E., Roberts M. S., Rodrigues Leite-Silva V. and Walters K. A., editors, CRC Press, 2019, or in similar reference books. Also, regulated cosmetic substances and ingredients are disclosed in the European Commission database "CosIng" (https://ec.europa.eu/growth/tools-databases/cosing).

Kojic acid active ingredient is in the form of capsules in the present invention, as disclosed above. Other active ingredients present in the formulation can also be encapsulated, for example in the form of liposomes.

Uses

As shown in example 5, it was surprisingly found that the reduction of the melanin content in reconstructed human pigmented epidermis treated with the combination of sclareolide, ascorbyl glycoside and kojic acid encapsulated in microcapsules or nanocapsules as defined in the present invention, having a MC1R agonistic peptide on their surface, is remarkably stronger than that that would be expected with a simple additive effect of the melanin supressing effects of each component, i.e., a clear synergistic effect between those ingredients was found by the inventors of the present invention.

Therefore, such composition is particularly useful for cosmetic use as skin-whitening agent.

Furthermore, in a clinical study performed with 30 healthy women having non-pathological facial blemishes (see example 6) it was concluded that the composition of the invention was highly effective for removing the spots and it was also safe since no adverse effects were reported.

Another aspect of the invention is, therefore, the cosmetic use (non-therapeutic) of the composition of the invention for skin whitening.

Another aspect of the invention is a method for skin whitening comprising the steps of topically applying an amount cosmetically effective of the composition of the invention to the subject in need thereof.

Specific uses included in the skin whitening effect are the elimination or reduction of hyperpigmented marks on the skin (spots, blemishes), or the smoothing uneven skin tone. The reduction of the marks may mean the reduction of the number of marks and/or the reduction of the size of the marks and/or lightening the intensity of the colour of the marks. Said hyperpigmented marks may be, for example, UV exposure related, post-scar marks, post-inflammation marks, melasma, lentigo or age-related marks, among others. The treated marks may be in any part of the body skin, preferably in the face, neck, arms and hands.

It is understood that the effect of the present composition is exclusively cosmetic, related to beautify and/or improve the feeling or sensory aspects o normal, nondiseased skin, in particular, intended to the removal of non-pathologic marks and not intended to prevent or ameliorate any disease.

Lentigines (lentigo in singular), for example, are asymptomatic small sharply circumscribed brown macules. They are commonly due to chronic sun exposure (solar lentigo, also called liver spots) and occur most frequently on the sun-exposed areas, particularly on the face, neck and back of the hands. They typically first appear during middle age and increase in number with age. One of the causes of solar lentigo is the aggregation of aged-cells containing a dark pigment called lipofuscin, resulting in the formation of dark spots. Lipofuscin is the product of the oxidation of lipids and proteins, which may be triggered by the UV radiation.

Melasma (also known as chloasma), for example, is the formation of irregular-shaped dark brown spots or patches of pigmentation on the face and other sun-exposed areas of the body. Melasma patches are asymptomatic and are only of cosmetic concern. Melasma is thought to be caused by sun exposure, genetic predisposition and hormone changes, and is particularly common in women, especially in pregnant women.

The compositions of the present invention may be applied topically once, twice, or more times daily. The composition is typically applied by spreading it over the skin, generally, only to over the skin area to be depigmented. The duration of the treatment may be adjusted to the type and intensity of the marks to be removed. Typically, the treatment may be maintained for several days (e.g. 5-10 days), several weeks (e.g. 1-6 weeks), or months (e.g. 1-12 months).

A cosmetically effective amount means the amount necessary of the composition to achieve the desired whitening effect. A skilled in the art can easily determine the amount of composition to be used in each administration.

EXAMPLES

Example 1A Preparation of a Composition According to the Invention

A composition according to the present invention was prepared using the components listed in the following table:

| | Ingredients | Weight % |
|---|---|---|
| A1 | Deionized water | q.s. 100% |
| A2 | Preservatives (Methylpropanediol, Caprylyl Glycol and phenyl-propanol) | 2.5 |
| A3 | Glycereth-26 | 5.0 |
| A4 | Phenoxyethanol | 0.8 |
| A5 | Bis-PEG-18 Methyl Ether Dimethyl Silane | 1.0 |
| B1 | SIMULGEL ™ INS 100 (Hydroxyethyl Acrylate/Sodium Acryloyldimethyl Taurate Copolymer, Squalane and Polysorbate 60) | 2.0 |
| B2 | Cyclopentasiloxane | 5.0 |
| B3 | Caprylic/capric Triglyceride | 2.0 |
| B4 | Sclareolide | 0.2 |
| B5 | Perfume | 0.1 |
| C1 | Deionized water | 3.96 |
| C2 | Ascorbyl glucoside | 2.00 |
| C3 | Disodium citrate | 0.14 |
| C4 | Disodium EDTA | 0.01 |
| C5 | Aqueous NaOH 50% | 0.56 |
| D4 | Solution of encapsulated kojic acid (kojic acid content) | 2.00 (0.0006) |
| | Total | 100.0 |

The components of the composition were commercially available. Sclareolide was available from the company Symrise (SymBright™ 2036). The solution of encapsulated kojic acid was prepared in advance as disclosed below.

The targeted microcapsules of kojic acid used for preparing the solution were bilayered microcapsules wherein the inner polymer was (D,L-lactide-co-glycolide) (PLGA) and the outer polymer was polyvinyl alcohol (PVA), said capsules had attached to the surface the peptide Palmitoyl-Ser-Tyr-Ser-Nle-Glu-His-DPhe-Arg-Trp-Gly-Lys-DPro-Val-NH—(CH$_2$)$_3$—(OCH$_2$CH$_2$)$_2$—CH$_2$—NH$_2$ (Peptide-I) which was coupled to the capsule by means of an amide bond between the amino terminal group of the peptide and the carboxylic groups available on the surface of the capsule from PLGA. Said microcapsules were prepared using a method analogous to that disclosed in example 1 of the international patent application WO-A-2015/075116.

Those targeted kojic acid microcapsules were incorporated into the composition in the form of an aqueous solution having the following composition:

| Ingredients | % (w/w) |
|---|---|
| PLGA | 0.03-0.05 |
| PVA | 0.015-0.025 |
| Peptide-I | 0.008-0.012 |
| Kojic Acid | 0.025-0.035 |
| Xanthan Gum | 0.40-0.60 |
| Phenoxyethanol | 0.40-0.60 |
| Caprylyl glycol | 0.25-0.40 |
| Glycerin | 0.04-0.06 |
| Glyceryl caprylate | 0.04-0.06 |
| Phenylpropanol | 0.025-0.04 |
| Water | q.s. 100% |

The proportion of kojic acid active substance in this solution is about 0.03% w/w. As this solution of encapsulated kojic acid was added in the composition at 2% weight percentage, the amount of kojic acid in the final compositions was of about 0.0006% (w/w) (6 ppm).

For preparing the composition, components A1-A5 were first mixed (component A5 was previously melted by heating at 50° C.) until obtaining a homogeneous mixture ("phase A"). Components B1-B5 were separately mixed until obtaining a homogeneous mixture, and it was added to phase A in a high-shear Ultra-Turrax homogenizer (about 2 minutes at 3000 rpm) and then in a paddle stirrer for about 15 minutes. Ingredients C1-C5 were mixed and added to the composition under stirring. Finally, component D4 was added. The pH of the final formula was checked to be in the range 5.5-6.5 (or otherwise adjusted with 10% citric acid or 10% NaOH).

The product obtained was a translucid-white aqueous dispersion.

Example 1B Preparation of a Composition According to the Invention

An analogous composition to that disclosed in example 1A was prepared, but also including saccharide isomerate to the composition.

The commercial product EPS White P (CODIF Technologie Naturelle) was used (containing water, glycerine, phenoxyethanol and 0.49% (w/w) of saccharide isomerate).

The composition was analogous to that disclosed in example 1A, but adding 1.0% of EPS White P (equivalent to 0.0049% (w/w) of saccharide isomerate), which was incorporated to the composition before the buffer components (C1-C5).

The product obtained was a translucid-white aqueous dispersion.

Example 2 Preparation of a Composition According to the Invention, with Enhanced Effect Against Spots Produced by Inflammatory Processes Another composition was prepared by adding the actives saccharide isomerate (EPS White P, CODIF Technologie Naturelle) and *Pancratium maritimum* extract (Neurolight 61 G, CODIF Technologie Naturelle, containing 0.3% (w/w) of *Pancratium maritimum* extract) to the synergistic combination of sclareolide-kojic acid-ascorbyl glucoside, to enhance its activity for removing spots produced by inflammatory processes.

The ingredients listed in the following table were used:

| | Ingredients | Weight % |
|---|---|---|
| A1 | Deionized water | q.s. 100% |
| A2 | Preservatives | 2.0 |
| | (Methylpropanediol, Caprylyl Glycol and phenylpropanol) | |
| A3 | Phenoxyethanol | 0.5 |
| A4 | Disodium EDTA | 0.1 |
| A5 | Anhydrous betaine extracted from sugar beet | 2.0 |
| A6 | *Oryza Sativa* starch | 2.0 |
| B1 | Polyacrylate crosspolymer-6 | 1.0 |
| B2 | Dibutyl adipate | 3.0 |
| B3 | Caprylic/capric Triglyceride | 2.0 |
| B4 | Sclareolide | 0.2 |
| B5 | Dimethicone/Vinyl Dimethicone Crosspolymer and Dimethicone | 3.0 |
| B6 | Diphenylsiloxy phenyl trimethicone | 5.0 |
| B7 | Cyclopentasiloxane | 3.0 |
| C1 | EPS White P | 1.0 |
| | (water, glycerine, phenoxyethanol and saccharide isomerate) | |
| | (saccharide isomerate content) | (0.0049) |
| C2 | Neurolight 61 G | 1.5 |
| | (Glycerin, water, and *pancratium maritimum* extract) | |
| | (*Pancratium maritimum* content) | (0.0045) |
| D1 | Deionized water | 3.97 |
| D2 | Ascorbyl glucoside | 2.00 |
| D3 | Disodium citrate | 0.13 |
| D4 | Disodium EDTA | 0.01 |
| D5 | Aqueous NaOH 50% | 0.65 |
| F1 | SEPIPLUS ™ 400 | 0.25 |
| | (Polyacrylate-13, Polyisobutene and Polysorbate 20) | |
| F2 | Solution of encapsulated kojic acid | 2.00 |
| | (kojic acid content) | (0.0006) |
| F3 | Perfume | 0.2 |
| | Total | 100.0 |

The components of the composition were commercially available. Sclareolide was available from the company Symrise (SymBright™ 2036). The solution of encapsulated kojic acid was prepared in advance as disclosed in example 1.

For preparing the composition, components A1-A6 were mixed in a paddle stirrer until obtaining a homogeneous mixture ("phase A"). Components B1-B7 were separately mixed until obtaining a homogeneous mixture, and it was added to phase A under stirring for about 15 minutes. Ingredients C1 and C2 were added one by one. Ingredients D1-D5 were mixed and added to the composition under stirring. The pH of the mixture was checked to be in the range 5.5-6.5 (or otherwise adjusted with 10% citric acid or 10% NaOH). Finally, the components F1, F2 and F3 were added one by one.

The composition obtained was a white aqueous cremigel.

Example 3 Preparation of a Composition According to the Invention, with Enhanced Effect Against Age-Related Spots A composition according to the invention was prepared by adding the actives saccharide isomerate (EPS White P, CODIF Technologie Naturelle), soy isoflavones (rich in genistein) and *Lepidium sativum* sprout extract (rich in sulforaphane) to the synergistic combination of sclareolide-kojic acid-ascorbyl glucoside, to enhance its activity for removing age-related spots.

A mixture of soy isoflavones and *Lepidium sativum* sprout extract is available from Mibelle AG (Delentigo™, containing about 0.11% (w/w) of genistein and about 0.14% (w/w) sulforaphane).

The ingredients of the composition are listed in the following table:

| | Ingredients | Weight % |
|---|---|---|
| A1 | Deionized water | q.s. 100% |
| A2 | Preservatives | 2.0 |
| | (Methylpropanediol, Caprylyl Glycol and phenylpropanol) | |
| A3 | Phenoxyethanol | 0.5 |
| A4 | Disodium EDTA | 0.1 |
| A5 | Anhydrous betaine extracted from sugar beet | 2.0 |
| A6 | *Oryza Sativa* starch | 2.0 |
| A7 | Potassium cetyl phosphate | 0.2 |
| B1 | Polyacrylate crosspolymer-6 | 1.0 |
| B2 | Dibutyl adipate | 3.0 |
| B3 | Caprylic/capric Triglyceride | 2.0 |
| B4 | Sclareolide | 0.2 |
| B5 | Dimethicone/Vinyl Dimethicone Crosspolymer and Dimethicone | 3.0 |
| B6 | Diphenylsiloxy phenyl trimethicone | 5.0 |
| B7 | Cyclopentasiloxane | 3.0 |
| C1 | EPS White P | 1.0 |
| | (water, glycerine, phenoxyethanol and saccharide isomerate) | |
| | (saccharide isomerate content) | (0.0049) |
| C2 | Delentigo ™ | 2.0 |
| | (water, polysorbate 80, alcohol, glycerine, lecithin, phenoxyethanol, soy isoflavones and *Lepidium sativum* sprout extract) | |
| | (genistein content) | (0.0022) |
| | (sulforaphane content) | (0.0028) |
| D1 | Deionized water | 3.97 |
| D2 | Ascorbyl glucoside | 2.00 |
| D3 | Disodium citrate | 0.13 |
| D4 | Disodium EDTA | 0.01 |
| D5 | Aqueous NaOH 50% | 0.65 |
| F1 | Solution of encapsulated kojic acid | 2.00 |
| | (kojic acid content) | (0.0006) |
| F2 | Perfume | 0.2 |
| | Total | 100.0 |

The components of the composition were commercially available. Sclareolide was available from the company Symrise (SymBright™ 2036). The solution of encapsulated kojic acid was prepared in advance as disclosed in example 1.

For preparing the composition, components A1-A6 were mixed in a paddle stirrer, heating at 40° C., until obtaining a homogeneous mixture ("phase A"). Components B1-B7 were separately mixed until obtaining a homogeneous mixture, and it was added to phase A under stirring. Ingredients C1 and C2 were added one by one. Ingredients D1-D5 were mixed and added to the composition under stirring. The pH of the mixture was checked to be in the range 5.5-6.5 (or otherwise adjusted with 10% citric acid or 10% NaOH). Finally, the components F1 and F2 were added one by one.

The composition obtained was a white aqueous cremigel.

Example 4 Preparation of a Composition According to the Invention, with Enhanced Effect Against Melasma A composition according to the invention was prepared by adding the actives saccharide isomerate (EPS White P, CODIF Technologie Naturelle) and *Lansium domesticum* leaf extract (DN-Aura®, BASF, containing about 25% (w/w) of Langstat extract) to the synergistic combination of sclareolide-kojic acid-ascorbyl glucoside, to enhance its effect against melasma pigmentation. A composition was prepared using the ingredients listed in the following table:

| | Ingredients | Weight % |
|---|---|---|
| A1 | Deionized water | q.s. 100% |
| A2 | Preservatives | 2.0 |
| | (Methylpropanediol, Caprylyl Glycol and phenylpropanol) | |
| A3 | Phenoxyethanol | 0.5 |
| A4 | Disodium EDTA | 0.1 |
| A5 | Anhydrous betaine extracted from sugar beet | 2.0 |
| A6 | *Oryza Sativa* starch | 2.0 |
| B1 | Polyacrylate crosspolymer-6 | 1.0 |
| B2 | Dibutyl adipate | 3.0 |
| B3 | Caprylic/Capric Triglyceride | 2.0 |
| B4 | Sclareolide | 0.2 |
| B5 | Dimethicone/Vinyl Dimethicone Crosspolymer and Dimethicone | 3.0 |
| B6 | Diphenylsiloxy phenyl trimethicone | 5.0 |
| B7 | Cyclopentasiloxane | 3.0 |
| C1 | EPS White P | 1.0 |
| | (water, glycerine, phenoxyethanol and saccharide isomerate) | |
| | (saccharide isomerate content) | (0.0049) |
| C2 | DN-Aura ® | 0.3 |
| | (Maltodextrin and *Lansium domesticum* leaf extract) | |
| | (*Lansium domesticum* extract content) | (0.075) |
| D1 | Deionized water | 3.97 |
| D2 | Ascorbyl glucoside | 2.00 |
| D3 | Disodium citrate | 0.13 |
| D4 | Disodium EDTA | 0.01 |
| D5 | Aqueous NaOH 50% | 0.65 |
| F1 | SEPIPLUS ™ 400 | 0.25 |
| | (Polyacrylate-13, Polyisobutene and Polysorbate 20) | |
| F2 | Solution of encapsulated kojic acid | 2.00 |
| | (kojic acid content) | (0.0006) |
| F3 | Perfume | 0.2 |
| | Total | 100.0 |

The components of the composition were commercially available. Sclareolide was available from the company Symrise (SymBright™ 2036). The solution of encapsulated kojic acid was prepared in advance as disclosed in example 1.

For preparing the composition, components A1-A6 were mixed in a paddle stirrer until obtaining a homogeneous mixture ("phase A"). Components B1-B7 were separately mixed until obtaining a homogeneous mixture, and it was added to phase A under stirring for about 15 minutes. Ingredients C1 and C2 were added one by one. Ingredients D1-D5 were separately mixed and added to the composition under stirring. The pH of the mixture was checked to be in the range 5.5-6.5 (or otherwise adjusted with 10% citric acid or 10% NaOH). Finally, the components F1, F2 and F3 were added one by one.

The composition obtained was a white aqueous cremigel.

Example 5 In Vitro Assay for Measuring Depigmentation

The depigmenting effect of the cosmetic composition of the invention was evaluated using the in vitro RHPE (Reconstructed human pigmented epidermis) model, as disclosed, for example in the article Sahuc F, Reconstructed human pigmented epidermis (rhpe): an in vitro model for the evaluation of melanogenesis, SOFW J., 2009, 135 (7), which is based on the quantification of the reduction of melanin content after daily topical application of the tested product on reconstructed human tanned epidermal tissue for 5-10 days. The reduction degree in melanin content achieved for each tested product is related to its depigmenting strength. The reconstructed human tanned epidermal tissue is composed of normal human keratinocytes cultivated in the presence of melanocytes (which can be of 3 different phototypes) localized in the basal layer. The different tanning degrees of these constructs correspond macroscopically to 3 different phototypes of human skin.

The test kit employed was obtained from the company Episkin (SkinEthic™ RHPE/Reconstructed Human Pigmented Epidermis). In particular, the phototype IV RHPE, size 0.5 $cm^2$ was used.

Each tested composition was topically applied, daily, for 5 days and subsequently the amount of melanin was quantified and the cell viability was tested. In general, more than one RHPE was used for each tested product for measuring melanin amount, and the mean value was then calculated. Furthermore, one additional RHPE was used for each tested composition for checking cell viability. 1 RHPE was used at the beginning of the test for measuring initial melanin content.

The tested compositions were prepared with the ingredients listed in the following table:

| | Ingredients | Weight % |
|---|---|---|
| A1 | Emulium ® Mellifera MB | 5.0 |
| | (polyglyceryl-6 distearate, jojoba esters, polyglyceryl-3 beeswax and cetyl alcohol) | |
| A2 | Isohexadecane | 2.0 |
| A3 | Isopropyl isostearate | 1.0 |
| A4 | Isopropyl myristate | 2.0 |
| A5 | Tocopheryl acetate | 0.2 |
| A6 | Sclareolide | (0.2) |
| B1 | Deionized water | q.s. |
| B2 | Potassium cetyl phosphate | 0.3 |
| B3 | Anhydrous betaine extracted from sugar beet | 2.0 |
| B4 | Preservatives | 2.0 |
| | (Methylpropanediol, Caprylyl Glycol and phenylpropanol) | |
| B5 | Phenoxyethanol | 0.5 |
| B6 | Disodium EDTA | 0.1 |
| B7 | Glycerin | 2.0 |
| B8 | Xanthan gum | 0.2 |
| C1 | SEPIPLUS ™ 400 | 0.5 |
| | (Polyacrylate-13, Polyisobutene and Polysorbate 20) | |
| C2 | Cyclopentasiloxane | 2.0 |
| C3 | Dimethicone | 1.0 |
| C4 | Perfume | 0.3 |
| D1 | Deionized water | 3.97 |
| D2 | Disodium citrate | 0.13 |
| D3 | Disodium EDTA | 0.01 |
| D4 | Aqueous NaOH 50% | 0.55 |
| D5 | Ascorbyl glucoside | (2.00) |
| E1 | Solution of encapsulated kojic acid | (2.00) |
| | (kojic acid content) | (0.0006) |
| | Total | 100.0 |

The active ingredients (sclareolide, ascorbyl glucoside and kojic acid) were selectively added to the formulation in order to prepare different compositions with different active ingredients, namely, either only one active was added, or binary combinations of kojic acid and one of the other actives, or a combination with the three actives, or a composition with no active ingredients, as reference. When an active was not added to the composition, equivalent weight of water was added to complete the stated percentages.

For preparing the composition, first components A1-A6 were heated to 70-75° C. and mixed to obtain a solution ("phase A"). Components B1-B8 were separately mixed to form a solution, which was heated to 70-75° C. Phase A was added to this solution and was emulsified in a high-shear Ultra-Turrax mixer (at 3000 rpm for 3 minutes, and then stirring at 300 rpm for about 10 minutes). The components C1-C3 were added at 60° C., the mixture was allowed to cool down to room temperature and C4 was then added. Ingredients D1-D5 were mixed and added to the previous mixture. Ingredient E1 was finally added. The final pH of the composition was checked to be in the range 5.5-6.5 (or otherwise adjusted with 10% citric acid or 10% NaOH).

For comparative purposes, a "base formulation", without any active ingredient, was prepared to be used as control composition. Thus, in this base formulation no active ingredients were added and the corresponding amounts of the substances in the formulation were adjusted with water.

Compositions 0-6 were prepared, containing the following combinations of active substances:

0. Base formulation (no actives)
1. Only kojic acid (6 ppm) (KA)
2. Only ascorbyl glucoside (2% w/w) (AG)
3. Only sclareolide (0.2% w/w) (S)
4. Kojic acid (6 ppm)+ascorbyl glucoside (2% w/w) (KA-AG)
5. Kojic acid (6 ppm)+sclareolide (0.2% w/w) (KA-S)
6. Kojic acid (6 ppm)+ascorbyl glucoside (2% w/w)+ sclareolide (0.2% w/w) (KA-AG-S)

The results of the depigmentation assays are shown in the following table:

| Comp. | n | Melanin (μg) | SD | Variation (exp.) | Variation (theor.) | Difference (exp. − theor.) |
|---|---|---|---|---|---|---|
| 0 | 4 | 33.26 | 0.34 | — | — | — |
| 1 (KA) | 6 | 32.72 | 0.31 | −0.54 | — | — |
| 2 (AG) | 6 | 32.78 | 0.29 | −0.48 | — | — |
| 3 (S) | 3 | 31.04 | 0.17 | −2.22 | — | — |
| 4 (KA-AG) | 6 | 32.89 | 1.30 | −0.37 | −1.02 | +0.65 |
| 5 (KA-S) | 4 | 30.44 | 0.60 | −2.82 | −2.76 | −0.06 |
| 6 (KA-AG-S) | 4 | 27.92 | 0.45 | −5.34 | −3.24 | −2.10 |

The information provided in the above table is the following:

The first column (Comp) identifies the composition assayed.

The second column (n) shows the sample size, i.e., the number of RHPE units used for each tested composition.

The third column (Melanin (μm)) shows the final melanin content (in micrograms) for each tested compound; the result shown is the mean of the results of all the samples.

The fourth column (SD) indicates the standard deviation of the mean value calculated in the preceding column.

The fifth column (Variation (exp)) shows the experimental variation found in the melanin content of the epidermis samples treated with each of the compositions 1 to 6 vs. the melanin content of samples treated only with a base composition (composition 0).

The sixth column (Variation (theor)) shows the calculated theoretical variation in the melanin content for the epidermis samples treated with the combination compositions 4 to 6 which would be expected with a simple additive effect of the melanin reduction provided experimentally by each of the single components of the combination (samples 1 to 3).

The seventh column (Difference exp.—theor.) shows the difference between the experimental melanin decrease found experimentally with the combined compositions (samples 4 to 6) and the theoretical melanin value to be expected with a simple additive effect of the components of the combination.

These results are graphically represented in FIG. 1.

It can be observed that the reduction in melanin content for samples treated with the composition 6, containing the combination of the three actives, i.e., kojic acid, ascorbyl glucoside and sclareolide, is greater than that that would be theoretically expected with a simple additive effect of the melanin suppression provided by the three actives individually. Therefore, a clear synergistic depigmenting effect was found with this combination.

Example 6 Clinical Study to Assess the Efficacy and Safety of the Composition of the Invention A prospective clinical study with 30 healthy women was performed to assess the depigmentation efficacy and the safety of the composition of the invention. The volunteers included in the study were 30-70 years old women having non-pathological facial blemishes or imperfections. The composition of Example 1B was applied twice daily, in the morning and evening, for 42 consecutive days, in a defined area, over the spots. A solar protector was also applied in the face once daily in the morning (SPF+50). Volunteers were visited at day 0, 14, 28 and 42 (end of the study).

Primary assessments were:
1) presence or absence of adverse effects;
2) decrease of the skin blemishes by measuring melanin; and
3) decrease of skin brightness in the blemishes.

Secondary assessments were subjective assessment by the volunteers of the efficacy and organoleptic properties of the product with a questionnaire.

Melanin was measured with the Mexameter® MX 18 and skin brightness was measured with Skin-Glossymeter GL 200 (Courage+Khazaka electronic GmbH).

No adverse effects were reported.

The values (mean) for melanin and brightness measured at the beginning (day 0) and after treatment (day 42), as well as the variation in those values (valueD42-valueD0) are shown in the following table:

|  | Day-0 | Day-42 | Variation | p-value* |
|---|---|---|---|---|
| Melanin | 214.4 | 164.9 | −49.5 (−23.1%) | 0.0001 |
| Brightness | 4.33 | 3.55 | −0.78 (−18.0%) | 0.0128 |

(*student's t test)

The questionnaire answered by the volunteers after completing the study included 25 questions for rating different aspects of the composition, including its perfume, spreadability, package, freshness, etc. The results of the questions specifically related to the depigmenting effect are shown in the following table:

|  | Totally agree | Agree | Disagree | Totally disagree |
|---|---|---|---|---|
| The product has reduced my skin spots | 16.7% (5) | 56.7% (17) | 26.7% (8) | 0.0% (0) |
| After using the product, the skin is brighter | 16.7% (5) | 60.0% (18) | 23.3% (7) | 0.0% (0) |

-continued

| | Totally agree | Agree | Disagree | Totally disagree |
|---|---|---|---|---|
| After using the product, the skin tone is smoother | 16.7% (5) | 60.0% (18) | 23.3% (7) | 0.0% (0) |
| After using the product, the skin looks younger | 13.3% (4) | 56.7% (17) | 30.0% (9) | 0.0% (0) |

Example 7 Composition Containing Sclareolide in the Form of Liposomes

An in vitro assay for assessing the depigmentation effect, as described in example 5, was performed using compositions with the following combination of actives:

0. Control (no product applied)
    1. KA-AG-SI-S
    2. KA-AG-SI-lipoS (6.67%)
    3. KA-AG-SI-lipoS (3%)
    4. KA-AG-SI-lipoS (1%)

wherein "KA" means encapsulated kojic acid solution (2% w/w, as disclosed in example 1, equivalent to about 6 ppm of kojic acid), "AG" means 2% w/w ascorbyl glucoside, "SI" means saccharide isomerate as 1% EPS White P (equivalent to about 0.0049% w/w saccharide isomerate), "S" means 0.2% w/w sclareolide, and "lipoS" means sclareolide in the form of liposomes. The concentration of the sclareolide liposomes of 6.67% w/w is equivalent to about 0.2% w/w sclareolide, the concentration of the liposomes of 3% w/w is equivalent to about 0.09% w/w sclareolide, and the concentration of 1% of the liposomes is equivalent to about 0.03% w/w sclareolide.

The liposomes of sclareolide were prepared using phosphatidylcholine and cholesterol as membrane-forming lipids.

The formulation and manufacturing method of the compositions were analogous as disclosed in example 5. The compositions containing sclareolide in the form of liposomes were more easily prepared, compared to those where sclareolide was not encapsulated, due to the good dispersibility of the liposomes in the aqueous phase.

The same test kit as in example 5 was used (SkinEthic™ RHPE/Reconstructed Human Pigmented Epidermis, phototype IV RHPE, size 0.5 cm², Episkin).

Each tested composition was topically applied, daily, for 5 days and subsequently the amount of melanin was quantified and the cell viability was tested (more than one RHPE was used for each tested product for measuring melanin amount, and the mean value was then calculated).

The results of the melanin content assay are shown in the following table, wherein the second column shows the final melanin content (in micrograms, mean value) for each tested composition and for the control (RHPE samples not treated) and the third column shows the calculated decrease of melanin content (in %) for treatments 1 to 4 vs. the control:

| Composition | Melanin (µg) | Variation (%) | SD | SE |
|---|---|---|---|---|
| 0 Control | 11.14 | — | 0.15 | 0.07634 |
| 1 KA-AG-SI-S | 4.30 | −61.4 | 0.07 | 0.03301 |
| 2 KA-AG-SI-lipoS (6.67%) | 4.56 | −59.1 | 0.04 | 0.01633 |

-continued

| Composition | Melanin (µg) | Variation (%) | SD | SE |
|---|---|---|---|---|
| 3 KA-AG-SI-lipoS (3%) | 3.75 | −66.3 | 0.15 | 0.06179 |
| 4 KA-AG-SI-lipoS (1%) | 5.03 | −54.9 | 0.05 | 0.02553 |

Figure 2:
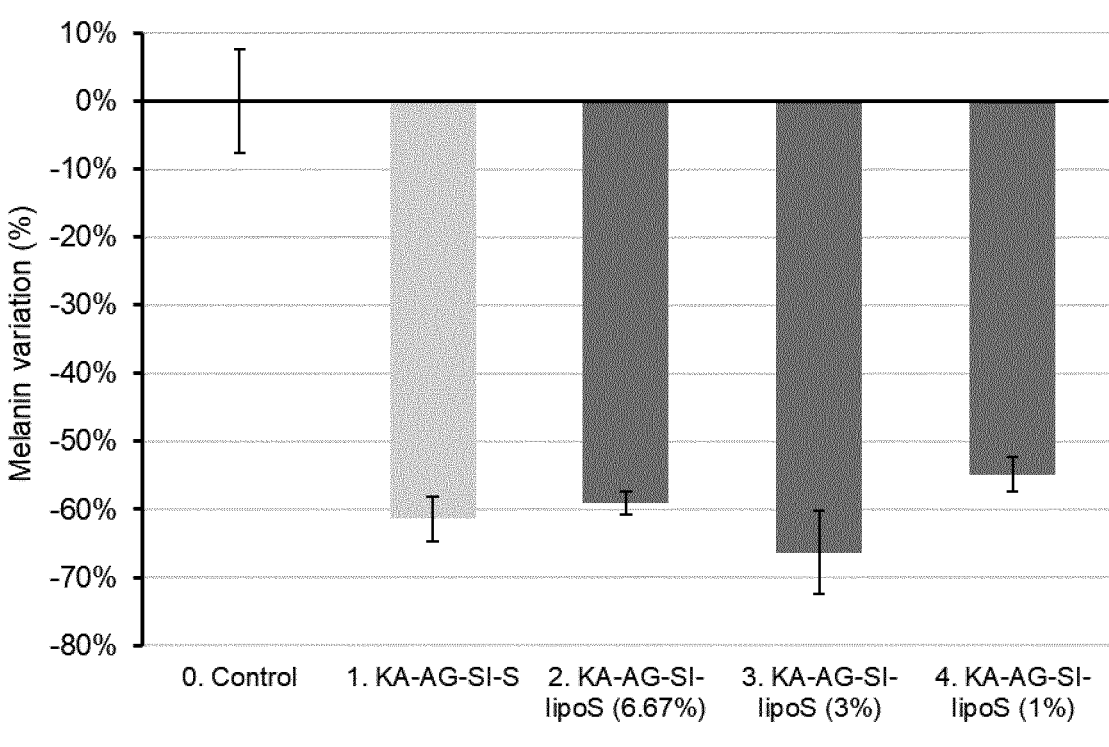
FIG. 2 shows a graph that represents the results of the in vitro depigmentation assay of example 7, using the same in vitro RHPE model ("Reconstructed human pigmented epidermis") for assessing the effect on the depigmenting efficacy of the compositions of encapsulating sclareolide within liposomes. Four different compositions (1 to 4) were tested, comprising encapsulated kojic acid (0.00006% w/w of kojic acid), ascorbyl glucoside (2% w/w), saccharide isomerate (0.0049% w/w) and sclareolide: composition 1 comprised 0.2% (w/w) non encapsulated sclareolide, while compositions 2, 3 and 4 comprised liposome-encapsulated sclareolide comprising 0.2% (w/w), 0.09% (w/w) and 0.03% (w/w) sclareolide, respectively. Composition 0 was the control (no product applied to the RHPE models). y-axis shows the melanin content variation (in %) after the 5-days treatment period and the x-axis shows the different compositions assayed.

The results are graphically represented in FIG. 2.

The results of the cell viability assay are shown in the following table, wherein the cell viability of the control (non-treated samples of epidermal tissue) was assigned to 100% viability, and the other compositions were rated relative to this reference.

| Composition | Cell viability | SD | SE | % | Error % |
|---|---|---|---|---|---|
| 0 Control | 0.706 | 0.016 | 0.012 | 100 | 1.6 |
| 1 KA-AG-SI-S | 0.681 | 0.013 | 0.010 | 97 | 1.3 |
| 2 KA-AG-SI-lipoS (6.67%) | 0.723 | 0.004 | 0.003 | 102 | 0.4 |
| 3 KA-AG-SI-lipoS (3%) | 0.795 | 0.029 | 0.020 | 113 | 2.9 |
| 4 KA-AG-SI-lipoS (1%) | 0.754 | 0.034 | 0.024 | 107 | 3.4 |

Figure 3:
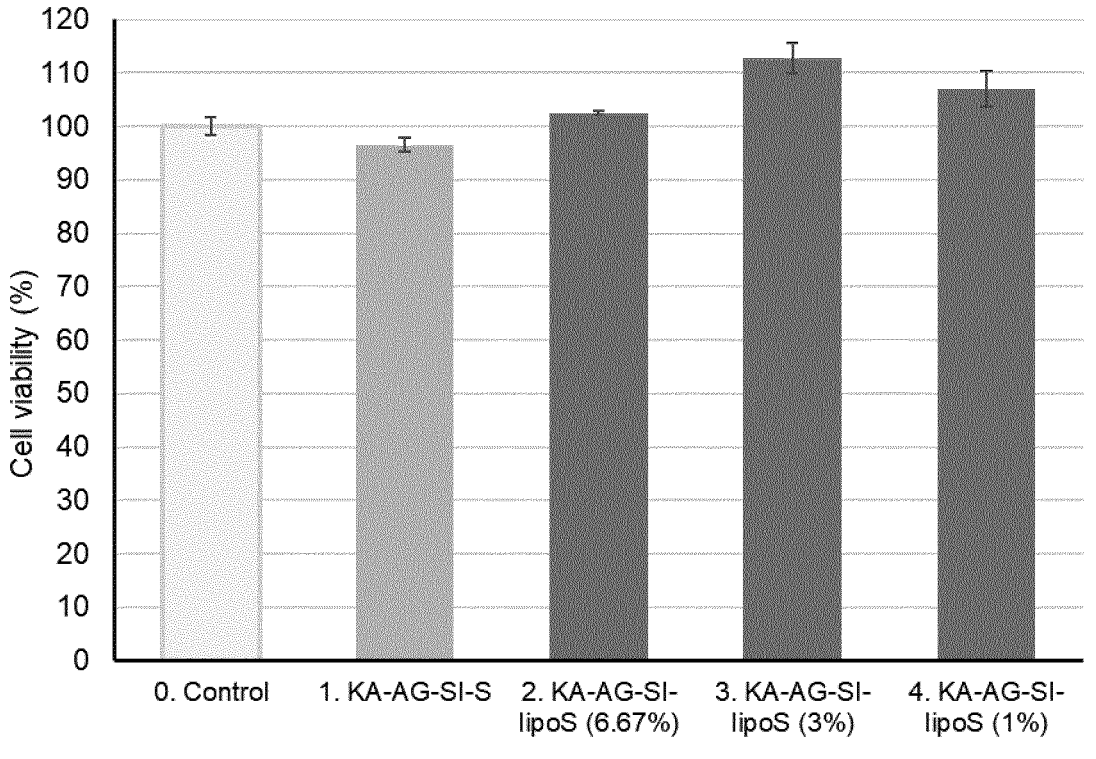
FIG. 3 represents the results of the cell viability test for the compositions assayed in example 7 (control composition 0 and compositions 1-4). Cell viability is expressed in % (y-axis) referred to the cell viability of the control composition, which is taken as the 100%.

The results of the cell viability assay are graphically represented in FIG. 3.

The results obtained in the assays show that when sclareolide was added in the form of liposomes, the results of the cell viability assay were superior for all assayed concentrations.

Furthermore, it was found that the effect on melanin reduction was greater when sclareolide was used as liposomes at 3% w/w (0.09% w/w sclareolide) compared to sclareolide not encapsulated (0.2% w/w sclareolide), i.e., greater depigmenting effect was achieved with less active skin-whitening substance.

The invention claimed is:

1. A skin-whitening composition comprising:
    (a) sclareolide;
    (b) kojic acid; and
    (c) ascorbyl glucoside;
    wherein kojic acid is encapsulated within a microcapsule or nanocapsule comprising a peptide of formula (I):

$$R_2\text{-Ser-Tyr-Ser-Nle-Glu-His-DPhe-Arg-(AA)-Gly-Lys-DPro-Val-}R_1 \qquad (I)$$

wherein:
      $R_1$ is the radical $-NH-(CH_2)_3-O-(CH_2CH_2O)_n-(CH_2)_3-NH_2$, wherein n is an integer from 1 to 10;
      $R_2$ is selected from $(C_{1-24}$ alkyl)-CO—, $(C_{2-24}$ alkenyl)-CO— and $(C_{6-10}$ aryl)-CO—; and
      AA is an amino acid containing an aromatic group;
    and cosmetically acceptable salts and solvates thereof,
    wherein the peptide is coupled to the outer surface of the microcapsule or nanocapsule, and
    wherein the content of kojic acid in the composition is comprised in the range 0.0001% (w/w)-0.01% (w/w).

2. The composition according to claim 1, characterized in that the content of kojic acid is comprised in the range 0.0001%-0.001% (w/w).

3. The composition according to claim 1, characterized in that n is 1 or 2.

4. The composition according to claim 1, characterized in that $R_2$ is selected from acetyl, propanoyl, pentadecanoyl, hexadecanoyl and heptadecanoyl.

5. The composition according to claim 1, characterized in that AA is selected from tryptophan, 3-(2-naphthyl)-D-alanine, 3-amino-3-(1-naphthyl)-propionic acid, 3-amino-3-

US 12,622,857 B2

25

(biphenyl)-propionic acid, phenylalanine, tyrosine, histidine, 5-hydroxytryptophan and L-3,4-dihydroxyphenylalanine.

6. The composition according to claim 1, characterized in that the amount of sclareolide in the composition is comprised in the range 0.001%-5% (w/w).

7. The composition according to claim 1, characterized in that sclareolide is encapsulated in the form of liposomes.

8. The composition according to claim 1, characterized in that the amount of ascorbyl glucoside in the composition is comprised in the range 0.01%-10% (w/w).

9. The composition according to claim 1, characterized in that it also comprises saccharide isomerate.

10. The composition according to claim 9, characterized in that the amount of saccharide isomerate in the composition is comprised in the range 0.00001%-2% (w/w).

11. The composition according to claim 1, characterized in that it also comprises genistein and suforaphane.

12. The composition according to claim 1, characterized in that it also comprises *Pancratium maritimum* extract.

13. The composition according to claim 1, characterized in that it also comprises *Lansium domesticum* (Langstat) leaf extract.

14. A method for skin whitening in a subject comprising the steps of topically applying an amount cosmetically effective of the composition of claim 1 to the subject.

15. The method according to claim 14 for the elimination or reduction of hyperpigmented marks of the skin.

16. The method according to claim 15, wherein the hyperpigmented marks of the skin are selected from the group consisting of UV exposure related marks, post-scar marks, post-inflammation marks, melasma marks, lentigo marks and age-related marks.

* * * * *